United States Patent
Tien et al.

(10) Patent No.: US 7,687,084 B2
(45) Date of Patent: Mar. 30, 2010

(54) COOL-PET SYSTEM

(76) Inventors: Linsheng W. Tien, 8 Arbusto, Irvine, CA (US) 92606; Kevin Tien, 8 Arbusto, Irvine, CA (US) 92606

(*) Notice: Subject to any disclaimer, the term of this patent is extended or adjusted under 35 U.S.C. 154(b) by 0 days.

(21) Appl. No.: 12/187,374

(22) Filed: Aug. 6, 2008

(65) Prior Publication Data
US 2009/0042984 A1   Feb. 12, 2009

Related U.S. Application Data

(60) Provisional application No. 60/954,314, filed on Aug. 6, 2007.

(51) Int. Cl.
*A61K 36/534* (2006.01)
*A01N 65/00* (2006.01)
*C12J 1/00* (2006.01)

(52) U.S. Cl. .................... 424/736; 424/747; 426/17
(58) Field of Classification Search .............. None
See application file for complete search history.

(56) References Cited

U.S. PATENT DOCUMENTS

| | | | |
|---|---|---|---|
| 2005/0031550 A1* | 2/2005 | Busch | 424/49 |
| 2005/0112259 A1* | 5/2005 | Qvyjt | 426/534 |
| 2006/0105025 A1* | 5/2006 | Hill et al. | 424/442 |
| 2006/0216365 A1* | 9/2006 | Nassif et al. | 424/736 |

* cited by examiner

*Primary Examiner*—Christopher R. Tate
*Assistant Examiner*—Deborah A. Davis
(74) *Attorney, Agent, or Firm*—WPAT, P.C.; Anthony King

(57) ABSTRACT

Included is an invention that deals with animal and pet nuisance, behavior control, obedience training, urinary and potty training, and repellent/discouragement method where a solution having vinegar and flavors being dispensed from a spray bottle is found to be effective in stopping or discouraging dogs, birds or animals from being noisy, being hyperactive, and behaving badly. The solution is also useful for obedience training purposes and can also be applied as a repellent/discouragement method when sprayed onto desired spots or onto the animal.

9 Claims, No Drawings

COOL-PET SYSTEM

CROSS-REFERENCE TO RELATED APPLICATIONS

This application claims priority to U.S. Provisional Pat. No. 60/954,314, filed on Aug. 6, 2007, now pending, which is hereby incorporated by reference in its entirety.

Although incorporated by reference in its entirety, no arguments or disclaimers made in the provisional application apply to this divisional application. Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

BACKGROUND OF THE INVENTION (1) Field of the Invention

The field of the invention relates to animal nuisance, behavior control, obedience training, urinary and potty training, and repellent system.

(2) Description of Related Art

There have been many attempts to quiet overly noisy pet dogs. Typical system includes electric shock collar that shocks the dog when the dog barks. Such device is inhumane. Other current marketed products such as collars with ultrasonic fittings or collars with attached spray bottles are unfriendly to the animals, are not portable (i.e. dogs have to always wear the devices), and are costly to maintain. Also, some sprays are formulated with hot pepper ingredients that can cause serious burns to the animal's nose and face.

Besides a need to control barking of dogs, there also remains a need to stop, discourage and control dog hyperactivity and bad behaviors. There is also a need for a product which can be used for obedience training purposes. An effective, simple, portable, natural, economic, friendly, and environmentally safe product formulated from food ingredients is ideal for these purposes.

In addition, there have been no successful means to control overly noisy birds. There remains a need to quiet overly noisy birds. Most products on the market utilize ultrasonic emitting devices or plastic imitation of predators; these devices are not very effective. Other products include repellants formulated with strong organic solvents, which can be hazardous to the birds and the environment.

There also remains a need to stop, discourage, and control cat nuisance and bad behaviors; especially urinary problems. Most current products designed for these problems are formulated with strong organic solvents as expellants or hormones. These products are either animal or environmentally unfriendly and can be very expensive. A simple, effective, natural, animal friendly and environmentally friendly product is needed and expected for the current market.

There also remains a need to discipline hyperactivity and bad behaviors for various other pets (e.g. hamsters), and animals in the farms and zoos (e.g. horses, pigs, cattle, monkey, snakes, etc.).

There remains a need to control pet nuisance, hyperactivity and bad behaviors; and a product for uses in obedience training.

BRIEF SUMMARY OF THE INVENTION

The inventor has discovered solutions that contain certain percentage of vinegar and optional flavors that can be used to control barking of dogs, overly noisy birds, and other noise producing pets and animals. In addition, the solution can also be used to stop, discourage, and/or control animal hyperactivity/bad behaviors as well as be applied for obedience training purposes. The effectiveness of the solutions can be enhanced by increasing the concentration of vinegar or adding certain flavors depending on the usage for different animals in different ages, size, breeds, and conditions (e.g., indoors or outdoors). The solution "cools" or calms down pets and animals. Thus, the term Cool-Pet is used to describe application for pets in general. Cool-Dog is used to describe application to dogs, while Cool-Bird, is used to describe application to birds. Cool-Cat is used to describe application to cats; Cool-Potty is used for urinary and potty training and repellent purposes . . . etc.

DETAILED DESCRIPTION OF THE INVENTION

The invention and its various embodiments can now be better understood by turning to the following detailed description of the preferred embodiments, which are presented as illustrated examples of the invention defined in the claims. It is expressly understood that the invention as defined by the claims may be broader than the illustrated embodiments described below. It should also be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Dogs are sensitive to "smell" and "taste", but, in general, compared to other animals, dogs are more sensitive to the smell than they are to taste. Dogs do not like the acidity "smell" of vinegar, and they also dislike the acidity "taste" of vinegar. Therefore, this formula is twice as effective for its purposes. Moreover, some flavors in this special formula will also enhance this effect, such as peppermint and Lime/lemon flavors.

The solution is placed in a spray bottle or other dispenser for use. For dogs, simply spray the solution near the nose and face areas of a barking or bad behaved dog. An example of the product's usage is to hold Cool-Dog spray bottle 6-12 inches away from dog face and spray. The smell and taste from the solution will stop or discourage dogs from barking, hyperactivity, and bad behaviors. The solutions can be effective for hours, depending on the breed, size, and age of the dogs as well as the condition of applying, and the formulation strength. For birds, simply spray the solution near the beak and neck area of a bird. This stops chirping of the bird and each application can be effective for hours, depending on the type of birds. Similarly, it can be applied to other pets and animals in the same way.

For animal urinary and potty training purposes, e.g. cat urinary problem, a formulation with stronger concentration of vinegar and/or flavors will be used, since the spray is applied to the desired spots and not on the animal. A stronger concentration can be used to increase the effectiveness without hurting the animals and environment. The product can replace current repellents, which contains strong organic solvents and are unfriendly to the animals and the environment.

One unique invention in this product is that all ingredients used in the formulations are food grade or a better, USP grade which can be found in general food products. This means that this product is also safe, natural and friendly to animals and the environment. This is unlike most current market products, which contains strong organic solvents and/or hot peppers which are unsafe for the animals and the environment.

Not wishing to be bound by the following theories, the inventor has discovered that birds are more sensitive to the sense of taste, rather than smell. Therefore, a preferred formulation for birds will include more vinegar and less added flavor such as peppermint and/or lemon. As for dogs, dogs are more sensitive to smell, rather than taste. Thus, a preferred formulation for dogs will include more additional flavoring such as peppermint and lemon to enhance the vinegar effectiveness. Also, the addition of flavors can mask the vinegar scent for people who dislike the smell of vinegar.

Active Ingredients of this solution will be vinegar and can be with or without the addition of optional active ingredients—flavors of peppermint or mint or lemon or lime or combinations. The solution may optionally include flavors/masking agent, such as mint, peppermint, lemon, lime, grape, cherry, citric, orange, garlic, and mustard. Also it is optionally to include preservatives, such as, BAK (benzalkonium chloride), benzoic acid, sodium benzoate, and benzyl alcohol sorbic acid. Preservative may not be necessary if pH is approximately 3.0. To maintain better product (solution and flavors) stability, optionally included in the solution is buffer—citric acid, sodium citrate, boric acid, sodium borate, sodium acetate, sodium phosphate. Another optional additive is a humectant, sweetening and tonicity agent such as glycerin which can make animal feel more comfortable and friendly. Surfactant or stabilizer agents such as polysorbate 80. Also optional is a pH adjuster such as HCL and NaOH.

More Detailed Formulation:

For general treatment to animal nuisance, behavior control, hyperactivity, and obedience training purposes: Active ingredient: Vinegar (Acidity range from acetic acid concentration is 4-8% in general, typically 5% acidity in most vinegar used in food purpose, such as white vinegar).

For dog, other pets and animals: a range of vinegar concentration may use 3-5% or 5-10% or 5-30%, 5-50%. And/or with Flavors 0.01%-10% of peppermint or mint or lemon or lime or combinations For Bird: a range of vinegar concentration may use 3-5%, or 5-10%, or 10-20% or 10-30% or 10-40% or 5-50%. And/or with Flavors 0.01%-10% of peppermint or mint or lemon or lime or combinations Other non-active ingredients: with other optional Flavors (0.01%-10%), glycerin (0.1%-5%), buffers (0.05%-8%), preservative (0%-3%).

The pH range of the formulations is pH 2.4-7.0 which formulated by vinegar, flavors, buffers and preservatives.

Preferred solution should have the lowest concentration of active ingredient, while remaining effective for most breeds of birds, dogs or other animals. The most preferred solution consists of 3-30% of vinegar (i.e. 0.15-1.5% acidity) depending on the pet/animal's breed, age, size and condition (e.g. place to use—outdoors or indoors).

For animal urinary repellent and urinary & potty training purposes, a higher concentration of vinegar and/or flavors in the formulations is recommended. Active ingredient: Vinegar 10-70% (Acidity range: 0.5%-3.5.0%) and/or with flavors 0.01%-15% of peppermint or mint or lemon or lime or combinations. For dogs, cats and other animals: may use vinegar 3-5% or 5-10% or 5-20% or 5-30% or 10-30% or 20-40% or 30-50% or 40-60%, or 50-80% and/or with flavors 0.01%-15% of peppermint, mint, lemon, lime or combinations of flavors.

FORMULATION EXAMPLES

| Ingredients (%) | 1-1 | 1-2 | 2-1 | 2-2 | 3-1 | 3-2 | 3-3 |
|---|---|---|---|---|---|---|---|
| Vinegar | 5 | 10 | 5 | 10 | 5 | 10 | 5 |
| Flavor 1 (Peppermint) | 0.1 | 0.1 | 0.1 | 0.1 | 0.1 | 0.1 | 0.1 |
| Flavor 2 (Lemon) | 0.1 | 0.1 | 0.1 | 0.1 | 0.1 | 0.1 | 0.1 |
| Glycerin | | | 0.1 | 0.1 | 0.1 | 0.1 | 0.1 |
| Polysorbate-80 | | | 0.1 | 0.1 | 0.1 | 0.1 | 0.1 |
| Citric Acid, monohydrate | | | | | 0.05 | 0.05 | |
| Sodium Benzoate | | | | | 0.2 | 0.2 | 0.2 |
| Water | | | | | | | |
| pH | 3.12 | 2.92 | 3.08 | 2.99 | 3.85 | 3.70 | 4.07 |
| Osm | 70 | 108 | 82 | 120 | 112 | 149 | |

| Ingredients (%) | 1 | 2 | 3 | 4 | 5 | 6 |
|---|---|---|---|---|---|---|
| Vinegar | 7.5 | 7.5 | 7.5 | 7.5 | 7.5 | 7.5 |
| Flavor 1 (Peppermint) | 0.1 | 0.1 | 0.1 | 0.1 | 0.1 | 0.1 |
| Flavor 2 (Lemon) | 0.1 | 0.1 | 0.1 | 0.1 | 0.1 | 0.1 |
| Glycerin | 0.1 | 0.1 | 0.1 | 0.1 | 0.1 | 0.1 |
| Citric Acid, monohydrate | | 0.05 | 0.05 | 0.15 | 0.15 | 0.15 |

-continued

| Ingredients (%) | Formulation number | | | | | |
|---|---|---|---|---|---|---|
| | 1 | 2 | 3 | 4 | 5 | 6 |
| Sodium Benzoate | | | 0.1 | | 0.1 | 0.2 |
| Water | | | | | | |
| pH | 3.00 | 2.91 | 3.60 | 2.68 | 2.75 | 3.33 |
| Osm | | 109 | 117 | | | |

| | Formulation # | | | | |
|---|---|---|---|---|---|
| Ingredients | D-6 | D-7 | D-8 | D-9 | D-10 |
| Vinegar (Acidity) | 12.5% (0.625% Acidity) | 17.5% (0.875% Acidity) | 20% (1.0% Acidity) | 30% (1.5% Acidity) | 50% (1.5% Acidity) |
| Peppermint flavor | 0.2% | 0.86% | 0.7% | 0.5% | 0.7% |
| Lemon-Lime Flavor | 0.2% | 0.53% | 0.7% | 0.5% | 0.7% |
| Na-citrate, Citric Acid, monohydrate | 0.05% | 0.05% | 0.05% | 0.05% | |
| Sodium Benzoate | 100 ppm | 100 ppm | 100 ppm | 100 ppm | 100 ppm |
| Glycerin | 0.05% | 0.05% | 0.05% | 0.1% | 0.1% |
| pH | 3.15 | 3.14 | 3.11 | 3.16 | 2.95 |

Formulations based on w/v %
Vinegar sold in the market for food purpose is 5% acidity. (i.e., 5% concentration of pure acetic acid). The vinegar used for the formulations is based on the 5% acidity food grade vinegar.

| | Formulation # | | | | |
|---|---|---|---|---|---|
| Ingredients | C-1 | C-2 | C-3 | C-4 | C-5 |
| Vinegar (Acidity) | 10% (0.5% Acidity) | 10% (0.5% Acidity) | 10% (0.5% Acidity) | 5% (0.25% Acidity) | 30% (1.5% Acidity) |
| Peppermint flavor | 0.1% | 0.1% | | 0.3% | 0.1% |
| Na-citrate | | 0.05% | | | |
| Na-citrate | | | | | |
| Citric Acid | | | 0.15% | | |
| BAK | | 100 ppm | | 100 ppm | |
| HCL/NaOH | | | | | |
| pH | 2.95 | 3.69 | 2.71 | 3.11 | 2.8 |

Formulations based on w/v %

In another embodiment, these formulations are found to be effective for insect repellent. An additional and optional ingredient, oleic acid, can be included in the formulations for better effect.

In yet another embodiment, the formulation may include herbal ingredient in portions similar to natural flavors shown above in the table. Optionally, these herbal ingredients in similar portions as natural flavors, may replace natural flavors in the solution. Contemplated herbs include coptis, licorice, rhubarb, and other bitter-taste-producing herbs.

In another embodiment, these formulations are found to be effective for snore control in human. Typical snoring controls known in the market include nostril clips and adhesive strips. They are, however, only effective if the snoring sleeper agrees to wear them. In the instant invention, person sleeping next to the snoring sleeper can take proactive steps to alleviate nuisance created by the snoring sleeper by applying the formulated solution to the snoring sleeper. For example, when the sleeper begins snoring, the waking person may apply the solution to the snoring sleeper on the skin under the sleeper's nose, using a roller applicator (or a brush). A single application is found to be effective in stopping the snoring right away without waking the sleeper.

Thus, specific embodiments and applications of animal nuisance and behavior control formulation have been disclosed. It should be apparent, however, to those skilled in the art that many more modifications besides those already described are possible without departing from the inventive concepts herein. The inventive subject matter, therefore, is not to be restricted except in the spirit of the appended claims.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. In addition, where the specification and claims refer to at least one of something selected from the group consisting of A, B, C . . . and N, the text should be interpreted as requiring only one element from the group, not A plus N, or B plus N, etc.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

What is claimed is:

1. A spray for external use containing an aqueous solution to provide animal behavior and nuisance control, said aqueous solution having a formulation comprising effective amounts of:
   vinegar of no more than 50% based on weight/volume %;
   glycerin;
   a flavor;
   polysorbate-80;
   BAK (benzalkonium chloride); and
   water,
   wherein the formulation results in a solution having a pH of no more than 3.9.

2. The spray of claim 1, wherein the flavor is selected from one of peppermint, lemon, and lime.

3. The spray of claim 2, wherein the vinegar is no more than 30% based on weight/volume %.

4. The spray of claim 3, wherein the vinegar is no more than 20% based on weight/volume %.

5. The spray of claim 2, wherein the vinegar is no more than 15% based on weight/volume %.

6. The spray of claim 2, wherein the vinegar is no more than 10% based on weight/volume %.

7. The spray of claim 2, wherein the vinegar is no more than 7.5% based on weight/volume %.

8. The spray of claim 2, wherein the vinegar is no more than 5% based on weight/volume %.

9. The spray of claim 2 further comprising an herb of bitter taste, selected from the group consisting of coptis, licorice, and rhubarb.

* * * * *